United States Patent [19]

Lonchampt et al.

[11] Patent Number: 4,727,322
[45] Date of Patent: Feb. 23, 1988

[54] METHOD AND APPARATUS FOR MEASURING THICKNESS OF A TEST PART BY AN EDDY CURRENT SENSOR, WITHOUT CONTACT AND WITH LIFT-OFF COMPENSATION

[75] Inventors: Thierry Lonchampt, Antony; Gerard Y. Mangenet, Brunoy, both of France

[73] Assignee: Societe Nationale d'Etude et de Construction de Moteurs d'Aviation "S.N.E.C.M.A.", Paris, France

[21] Appl. No.: 809,785

[22] Filed: Dec. 17, 1985

[30] Foreign Application Priority Data

Dec. 19, 1984 [FR] France .................. 84 19409

[51] Int. Cl.$^4$ ........................ G01B 7/12
[52] U.S. Cl. .................. 324/229; 324/225; 324/207; 324/202
[58] Field of Search ........... 324/207, 208, 234, 236, 324/237–243, 262, 225, 226, 202, 233, 227, 229

[56] References Cited

U.S. PATENT DOCUMENTS

| | | | |
|---|---|---|---|
| 3,358,225 | 12/1967 | Peugeot | 324/225 |
| 3,496,458 | 2/1970 | Bromley | 324/225 |
| 3,718,855 | 2/1973 | Rogel et al. | 324/202 |
| 4,186,792 | 2/1980 | Yamada et al. | 324/207 X |
| 4,215,310 | 7/1980 | Schwerer, III | 324/225 |
| 4,314,203 | 2/1982 | Häberlein | 324/262 |
| 4,438,754 | 3/1984 | Nanny et al. | 324/207 X |
| 4,596,953 | 6/1986 | Nagasaka et al. | 324/207 X |
| 4,644,274 | 2/1987 | Casarcia | 324/225 X |

FOREIGN PATENT DOCUMENTS

| | | |
|---|---|---|
| 3324444 | 1/1984 | Fed. Rep. of Germany . |
| 178155 | 11/1982 | Japan . |
| 2082330 | 3/1982 | United Kingdom . |

Primary Examiner—Gerard R. Strecker
Assistant Examiner—Warren S. Edmonds
Attorney, Agent, or Firm—Oblon, Fisher, Spivak, McClelland & Maier

[57] ABSTRACT

A method of measuring a characteristic, such as thickness, of a test part makes use of the variation in impedance of a coil in a senor caused by eddy currents generated as a result of the proximity of the test part. The sensor measures two orthogonal components of the complex impedance. In use the sensor is moved towards the test part until one component of the impedance reaches a predetermined value and the characteristic measured as the value of the other component. The first component is selected during calibration as that component which is most sensitive to variation in the distance between the sensor and the test part.

3 Claims, 3 Drawing Figures

METHOD AND APPARATUS FOR MEASURING THICKNESS OF A TEST PART BY AN EDDY CURRENT SENSOR, WITHOUT CONTACT AND WITH LIFT-OFF COMPENSATION

BACKGROUND OF THE INVENTION

1. Technical Field

The present invention relates to a method of measuring a characteristic of a test part and also to apparatus for carrying out such a measurement by use of a sensor including a coil, the impedance of which is influenced by eddy currents induced in the test part.

The method and apparatus to be described allow non-destructive measurement of a variety of characteristics of test parts, for example the thickness of an electrically-conductive test part or of an electrically-conductive coating applied to the test part.

2. Prior Art

Existing eddy current sensors include a coil to which an alternating current of predetermined frequency is applied. The coil is also connected to a control apparatus for measuring the impedance of the sensor when the sensor is in contact with or adjacent to a test part. Eddy currents induced in the test part effect the impedance of the coil. The magnitude of the eddy currents generated depends on the nature of the test part, and also on the proximity of the sensor to the test part in a sophisticated manner which does not need to be fully understood for implementation of the invention.

The impedance of the coil is a vector which can be completely defined by measuring two orthogonal components of the impedance. Theoretically the impedance vector can be defined as a purely resistive component and as an orthogonal, purely reactive, component. The reactive component is frequency dependent and includes induction and capacitance effects. Known control apparatus for measuring two orthogonal components of the impedance vector do not, in general, allow recognition of the resistive and reactive components but, rather, provide for measurement of two, arbitrary orthogonal components. It is normally possible to adjust the control apparatus so that it measures components of the impedance in any two arbitrary orthogonal directions. Thus, the two reference axes of a control apparatus for measuring two orthogonal components may readily be adjusted in phase as required. It may also be possible to adjust the origin of the orthogonal reference axes in a translatory manner.

In the following discussion reference is made to Horizontal and Vertical-components of impedance. It will be appreciated that these are arbitrary, but variable, orthogonal directions.

If a sensor coil is supplied with an alternating frequency signal and the horizontal and vertical components of its impedance are measured and supplied to the X and Y inputs of an oscilloscope, the impedance measured is visualised on the oscilloscope screen as a dot. If the sensor coil is then brought towards an electrically conductive test part the point on the oscilloscope screen which represents the impedance traces a path on the screen. The trace produced on the oscilloscope screen as a result of the point traversing its path in time will be referred to hereinafter as the lift-off curve. The curve extends between two points. A first end point represents the impedance of the coil in space when it is not influenced at all by the presence of the test part. The other end point is the value of the impedance when the sensor coil is in contact with the test part.

Under predetermined operational conditions it is found that the length of this curve between the two points and its orientation relative to the first end point representing the impedance of the coil in space is a function of characteristics of the test part, and the distance between the sensor and the test part. For example, if the test part carries a non-electrically conductive coating on its surface then the resulting clearance between the sensor and the test part results in a curve of a length which varies as a function of the thickness of the layer. A layer of air between the test part and the sensor has a similar effect.

Other characteristics influence the location of the curve. For example, the magnetic permeability of the test part, its conductivity, the presence of fissures or defects in the material of the test part and the thickness of the test part all effect the location of the curve. In the case of determining the thickness of the test part, in particular, the influence is only measurable if the thickness of the test part is of the same order of magnitude as the depth of penetration of the eddy currents into the test part.

Hitherto, it has been proposed to use this type of sensor by bringing the sensor into contact with the test part and comparing the value of at least one component of the impedance measured at this point with a reference value. This technique has numerous disadvantages. Since the materials of which the sensor is made are generally fragile, rapid wear is apparent and a deterioration in the coil follows repeated shocks on the sensor. The pressure exerted at the end of the sensor can give rise to parasitic effects which falsify the measurements. The sensor, which is heated by the Joule effect is cooled by thermal exchange with the test part which is at ambient temperature. This temperature variation gives rise to parasitic effects. Further, if the axis of the sensor coil is not truly orthogonal to the test part then there will be an effective clearance between the coil and the test part which, in turn, effects the impedance measured.

It is possible to reduce certain of these disadvantages by adhering a strip of synthetic material to the tip of the sensor in order to protect it. Alternatively, the sensor coil can be displaced slightly to the rear of the tip of the sensor. However, these solutions result in a variability of the response of different sensors because of differences in the displacement of the coil from the sensor tip or the thickness of the protective synthetic material. This can falsify the measurements. With this type of solution recalibration and sensitive corrections are normally required.

DE-A No. 3 324 444 describes an eddy current sensor which is capable of effecting measurements without contact between the sensor and the test part. In this case, a differential sensor is used which has two coils which perform the double function of measuring the lift-off curve on the one hand and also monitoring a characteristic of the test part on the other hand. Such an apparatus allows measurement at any time of the error due to variation in the lift-off curve and uses a complex calculation function in order to correct this error during scanning of the test part.

SUMMARY OF THE INVENTION

It is an object of the invention to use the properties of the lift-off curve to measure a characteristic of a test part, which characteristic has an influence on the lift-off curve.

It is a further object to provide a sensor which is capable of taking single measurements on a test part or of scanning the test part.

The sensor of the invention is intended to enable measurement of, for example, any of the following characteristics:

(a) The measurement of the thickness of the walls of test parts, for example, hollow members such as turbine blades of a turbo-machine provided with internal cavities for the circulation of working fluid and produced by precision moulding with a ceramic core which is melted out after solidification of the part;

(b) Measurement of the thickness of an electrically-conductive coating deposited on the surface of a test part;

(c) Measurement of the spacing between electrically-conductive foils;

(d) Classifying materials;

(e) Control of thermal treatment;

(f) Testing a structural material for heterogeneity;

(g) Evaluation of structural changes caused by operation of parts; and (h) Detection of defects, such as cracks or voids in the material of a test part.

Yet a further object of the present invention is to provide a sensor which does not require contact between the sensor and the test part, and which does not require the double coils or complex calculation systems of the prior art differential sensor, while still enabling effective measurement.

The present invention accordingly provides a method of measuring a characteristic of a test part by means of a sensor including a coil having an impedance which is affected by the distance between said part and the sensor, and by variations in said characteristic, including the steps of measuring two orthogonal components of the impedance, positioning the sensor such that a first component of the measured impedance has a predetermined value, and measuring the characteristic as represented by the value of the second component, the first component being selected as that component which is more sensitive to variations in the distance between the sensor and the test part.

The invention further provides apparatus for carrying out the above defined method for measuring a characteristic of a test part, including a sensor having a coil, means for supporting the sensor such that it is movable substantially perpendicular to a tangent to a surface of the test part, a drive motor operatively connected to said sensor for moving it along said support means, eddy current control apparatus operatively connected with said sensor coil for measuring the impedance thereof, said eddy current control apparatus having first and second outputs each producing a respective signal representative of the first and the second of the two orthogonal components of the measured impedance, and a servo control system having a first input connected to said first output of said control apparatus, a second input for receiving a predetermined reference value, and an output connected to said drive motor such as to cause the drive motor to move the sensor towards the test part until a time when the values of the two inputs to the servo control system are substantially the same, the measure output of the eddy current apparatus being the value at the second output of the control apparatus at said time.

In practice it is found that the method and apparatus defined above allow the elimination of parasitic factors because contact between the sensor and the test part are not required. This results in the achievement of reliable results. Furthermore, the method of the invention can readily be practised automatically so that it is suitable for use in monitoring characteristics of a test part during manufacture.

An embodiment of the method and apparatus of the invention will now be described, by way of example.

DESCRIPTION OF A PREFERRED EMBODIMENT

Figure 1:
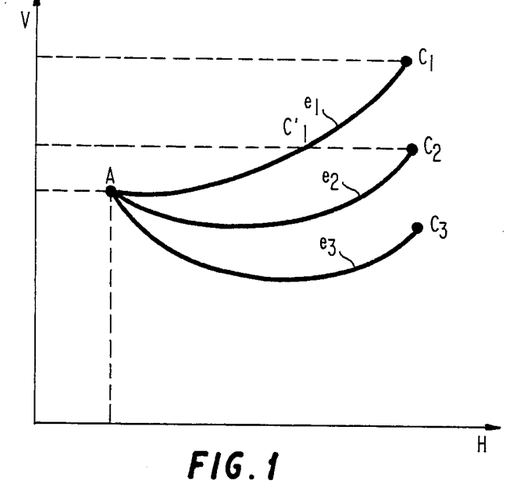
FIG. 1 shows a family of lift-off curves as produced by moving a sensor towards parts of various thicknesses.

A family of lift-off curves illustrating the impedance variation of a coil in an eddy current sensor as the sensor is moved uniformly from a position where it is substantially unaffected by the test part to a position in contact with the test part is shown in FIG. 1. Each curve illustrates how the vertical and horizontal components (these components being defined as in the prior art above mentioned) of the measured impedance vary as the sensor is brought towards a test part of a respective different thickness, $e_1$, $e_2$, or $e_3$. The curves diverge from a common point A which corresponds to the value of the absolute impedance of the coil when it is not affected by eddy currents generated in the test part. The phases of the vertical and horizontal components of the impedance measured are selected such that the curves are oriented substantially parallel to the horizontal axes. That is, the horizontal component of the impedance reflects the effect on the impedance of the spacing between the sensor and the test part to a far greater extent than the vertical component is affected by this spacing. When the sensor moves towards a part of thickness $e_1$ the impedance varies between the value A and the value $C_1$, which represents the value of the impedance at the contact point. The curves $AC_2$ and $AC_3$ are obtained similarly for test parts of thicknesses $e_2$ and $e_3$ respectively.

If the sensor is brought into contact with the part, it is true that different values are obtained for the vertical component of the impedance as illustrated in FIG. 1. From these values of the vertical component of impedance it would be possible to determine the thickness of the test part. However this approach suffers form the disadvantage that errors can be introduced if the sensor is slightly inclined with respect to the surface of the test part. For example, with a test part of thickness $e_1$, if the sensor is inclined relative to the perpendicular, it can come into contact with the test part at the point $C'_1$ on the curve $AC_1$ as shown in FIG. 1. At this point the magnitude of the vertical component of the inductance is the same as for a part of thickness $e_2$. Therefore the thickness of the part with thickness $e_1$ is erroneously measured as $e_2$.

An error of a similar kind can occur when the coil is retracted within a concentric sheath in order to eliminate certain parasitic effects due to the pressure between the sensor and the test produce. Suppose, for example, the sensor is replaced during monitoring of a batch of test parts and the first sensor had its coil displaced by a distance $D_1$ within its sheath and the second by a distance $D_2$ within its sheath. Inconsistant measurements will be made by the two sensors if this variation in the gap at "contact" is not taken account of.

Figure 2:
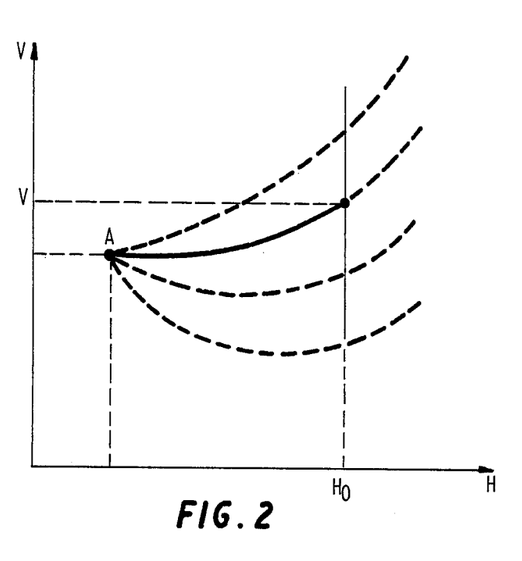
FIG. 2 illustrates a further family of curves such as in FIG. 1 for explaining the method of the present invention.

FIG. 2 illustrates a further family of lift-off curves for explaining the principle of the present invention. Once again these departure curves have been developed for test parts of varying thicknesses, and the phase of the horizontal component, and also necessarily of the vertical component, has been adjusted so that the curves tend to be generally aligned with the horizontal axis. Preferably, during calibration of the apparatus the family of curves is developed on an oscilloscope for the range of thicknesses under consideration. It will be noted that for each curve, as the sensor is brought towards the test part in a direction substantially normal to a tangent of the surface of the test part, the impedance varies from the value at A. These curves can be produced by supporting the sensor on an automatically driven means.

In order to measure the thickness of the test part in accordance with the invention, the sensor is moved towards the test part until the horizontal component of the impedance has a predetermined value $H_0$. The value $H_0$ is selected during preliminary calibration tests in order to produce a significant variation in the vertical component of impedance for parts of different thicknesses. As will be seen from FIG. 2 the value $H_0$ is achieved before the ends of the curves, that is before the sensor is in contact with the test part. The value of $H_0$ is generally close to but outside the range of values of H for the point at which the sensor is in contact with the test part for any thickness of the test part within the range to be measured. The movement of the sensor toward the test part is stopped when the measured value of the horizontal component of H reaches the value $H_0$. The sensor is then ready for measurement of the value of the vertical component V of the impedance at the point where the horizontal component has value $H_0$. This value can be simply related to the thickness of the test part. The relationship between the values of V and the thickness can readily be determined by calibrating the sensor with reference to a number of test parts of known thickness. Such a calibration stage can also be used to determine the appropriate value of $H_0$ which will ensure that the sensor is never brought into contact with any test part, thus eliminating the problems of parasitic effects and wear.

Figure 3:
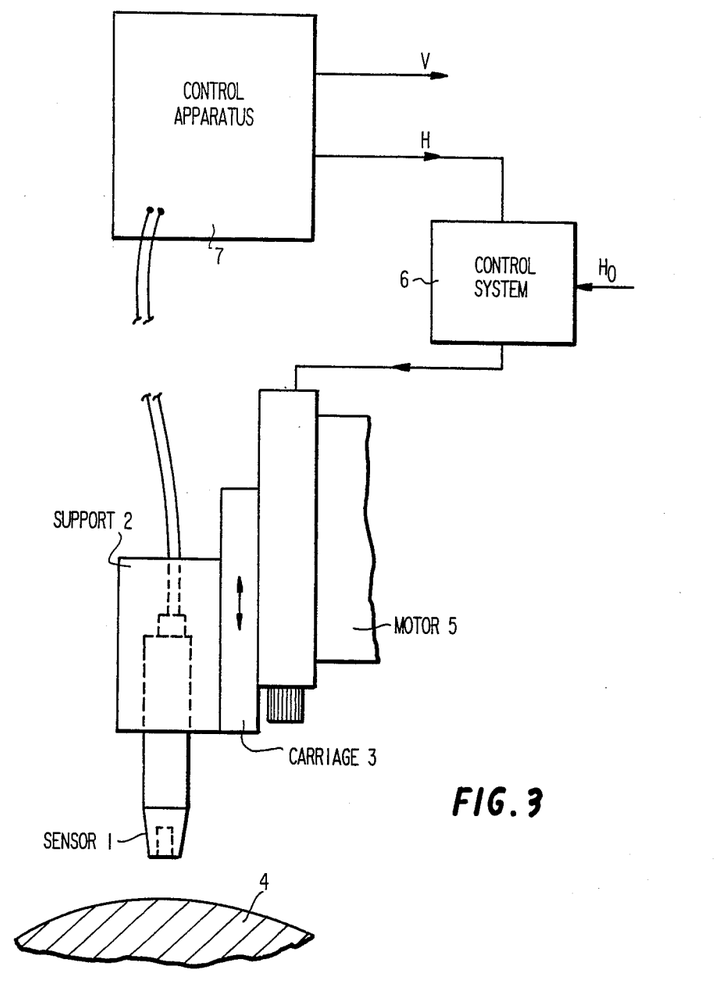
FIG. 3 is a diagrammatic representation of apparatus in accordance with the invention.

FIG. 3 illustrates in more detail a form of apparatus for carrying out the method described above.

As shown in FIG. 3 a sensor 1 including a coil is mounted in a support 2 including a carriage 3 which is movable transversely in the directions of the double headed arrow, that is in a direction perpendicular to a tangent to the surface of a test part 4, a characteristic of which, such as the thickness, is to be measured. The test part is normally mounted on a suitable support which may include a positioning device for bringing test parts sequentially into a position for measurement by the sensor. Such positioning devices are not shown in the drawing and may take any suitable form known to those skilled in the art, for example they may be manual or automatic and include programmed control.

The carriage 3 is operatively connected to an electric motor which allows it to be moved up and down. Control signals for the motor 5, which determine the motion of the carriage 3 and thus the support 2 and sensor 1, are provided by a control system 6 which may be constructed from known electronic components in a manner that will be readily apparent to those skilled in the art. The servo control system 6 has an input for the predetermined value $H_0$ and an input for the instantaneous value of H of the sensor 1. The control system compares the values of H and $H_0$ and, when these reach substantial identity the motor 5 is caused to stop. In between measurements, the control system 6 controls the motor 5 to retract the sensor to its start position away from the test part. This can conveniently be done as a new test part is brought into position below the sensor.

An eddy current control apparatus 7 is provided which is electrically connected to the coil of the sensor 1. The control apparatus 7 provides the necessary alternating current signal to the coil 1 and receives feedback from the coil 1 which allows it to output the values of two orthogonal components of the impedance of the coil. These values are output as V and H continuously during operation of the sensor. The control apparatus 7 is such that the phases of V and H can be adjusted in a known manner so that the horizontal component of the impedance is substantially aligned with the lift-off curves for the particular test parts to be measured as discussed previously.

In operation of the device, the phase of the V and H components of the control apparatus 7 and the value of the signal $H_0$ are determined during a calibration stage. This calibration stage may be carried out during production of the sensor or carried out by the user if the characteristic can be measured by the sensor is changed or the range of thicknesses to be measured, for example, is modified. The phase of H and the value of $H_0$ are selected by monitoring a family of lift-off curves on an oscilloscope as discussed with reference to FIG. 2.

When a characteristic such as the thickness of a test part 4 is to be measured, the servo control system 6 controls the motor 5 to retract the carriage 3 and, therefore, the sensor 1 on its support 2. The control apparatus 7 supplies an alternating signal to the coil of the sensor 1 and measures its impedance continuously as the control system 6 controls the drive motor 5 to move the sensor uniformly towards the test part 4. The servo control system 6 continuously compares the measured value of H with the reference value $H_0$ during this motion and stops the movement of the sensor 1 when the instantaneous value of H is substantially equal to $H_0$. At this time the value of V represents the value of the characteristic to be measured and is fed out from the control apparatus 7. Once the measurement is completed the servo control system 6 retracts the sensor and a new test part is brought into position for a further measurement.

Various modifications may be made to the method and apparatus described within the spirit of the present invention. For example it is possible to use a control system other than that which has been described. It is not necessary for the operation of the servo control system to be automatic and the comparison between the value of H and $H_0$ could be made manually. Instead of controlling the motor 5 to continuously move the sensor 1 it is possible to displace the sensor incrementally. This is particularly advantageous when the control apparatus and control system are embodied in a computer together with appropriate power supplies. Although the embodiment has been discussed with particular reference to measurement of thickness of test parts, it will be appreciated that various other characteristics which affect the impedance of the coil can readily be measured using the described method and apparatus.

Instead of making a single measurement on each test parts, multiple measurements can be made at different points on the same test part.

We claim:

1. A method of measuring a thickness, of a test part by means of a sensor including coil having an impedance which is affected by the distance between said part and the sensor, and by variations in said thickness, including:
   a calibration step including measuring the variation of the two measured components of impedance as the sensor is moved towards a calibration part, for a plurality of calibration parts each having a different value of thickness within the expected range of said thickness in the test parts, selecting the phases of the vertical and horizontal components of the measured impedance such that the curves of said impedance are oriented substantially parallel to one of the axes and selecting a first of the two components and a predetermined value from said first component such that the predetermined value is achieved close to but spaced from the position where the sensor is in contact with the test part for values of the thickness within the expected range,
   a step of measuring the two orthogonal components of the impedance of the coil during test part examination,
   and a step of positioning the sensor by means of a servocontrol system connected to a drive motor such that the first of the two components of the measured impedance has the predetermined value and measuring the thickness of the test part as represented by the value of the second of the two components, the first component being selected as that component which is more sensitive to variations in the distance between the sensor and the test part.

2. A method as claimed in claim 1, further including the step of moving the sensor towards the test part from a distance where the presence of the test part has substantially no effect in the impedance of the coil towards a position where said first component has said predetermined value.

3. Apparatus for measuring the thickness of a test part comprising:
   a sensor having a coil,
   means for supporting the sensor such that it is movable substantially perpendicular to a tangent to a surface of the test part,
   a drive motor operatively connected to said sensor for moving it along said support means,
   an eddy current apparatus operatively connected with said sensor coil for measuring the impedance thereof, said eddy current apparatus having first and second outputs each producing a respective signal representative of the first and the second of the two orthogonal components of the measured impedance, and
   a servo-control system having a first input connected to said first output of said eddy current apparatus, a second input for receiving a predetermined reference value, and an output connected to said drive motor such as to cause the drive motor to move the sensor towards the test part until a time when the values of the two inputs to the servo-control system are substantially the same, wherein the value at the second output of the eddy current apparatus at said time represents said thickness of said test part.

* * * * *

UNITED STATES PATENT AND TRADEMARK OFFICE
CERTIFICATE OF CORRECTION

PATENT NO. : 4,727,322

DATED : FEBRUARY 23, 1988

INVENTOR(S) : Thierry LONCHAMPT ET AL

It is certified that error appears in the above-identified patent and that said Letters Patent is hereby corrected as shown below:

In the Abstract, line 3, delete "senor" and insert therefor --sensor--.

Column 1, line 25, delete "effect" and insert therefor --affect--;

Column 1, line 51-52, delete "Horizontal and Vertical-components" and insert therefor --horizontal and vertical-components--;

Column 1, line 59, delete "visualised" and insert therefor --visualized--;

Column 1, line 60-61, delete "electrically conductive" and insert therefor --electrically-conductive--;

Column 1, line 66, delete "end point" and insert therefor --endpoint--.

UNITED STATES PATENT AND TRADEMARK OFFICE
CERTIFICATE OF CORRECTION

PATENT NO. : 4,727,322

DATED : FEBRUARY 23, 1988

INVENTOR(S) : Thierry LONCHAMPT ET AL

It is certified that error appears in the above-identified patent and that said Letters Patent is hereby corrected as shown below:

Column 2, line 1, delete "end point" and insert therefor --endpoint--;

Column 2, line 5, delete "end point" and insert therefor --endpoint--;

Column 2, line 9, delete "non-electrically conductive" and insert therefor --non-electrically-conductive--;

Column 2, line 19, delete "effect" and insert therefor --affect--;

Column 2, line 42, delete "effect" and insert therefor --affect--.

Column 3, line 64, delete "servo control" and insert therefor --servo-control--.

UNITED STATES PATENT AND TRADEMARK OFFICE
CERTIFICATE OF CORRECTION

PATENT NO. : 4,727,322

DATED : FEBRUARY 23, 1988

INVENTOR(S) : Thierry LONCHAMPT ET AL

It is certified that error appears in the above-identified patent and that said Letters Patent is hereby corrected as shown below:

Column 4, line 2, delete "servo control" and insert therefor --servo-control--;

Column 4, line 11, delete "practised" and insert therefor --practiced--;

Column 4, line 21, start a new paragraph beginning at "FIG. 2";

Column 4, line 60, delete "form" and insert therefor --from--;

Column 4, line 67, delete "inductance" and insert therefor --impedance--.

Column 5, line 10, delete "Inconsistant" and insert therefor --Inconsistent--;

Column 5, line 15, delete "departure" and insert therefor --lift-off--.

UNITED STATES PATENT AND TRADEMARK OFFICE
CERTIFICATE OF CORRECTION

PATENT NO. : 4,727,322

DATED : FEBRUARY 23, 1988

INVENTOR(S) : Thierry LONCHAMPT ET AL

It is certified that error appears in the above-identified patent and that said Letters Patent is hereby corrected as shown below:

Column 6, line 11, delete "servo control" and insert therefor --servo-control--;

Column 6, line 39, delete "can be";

Column 6, line 45, delete "servo control" and insert therefor --servo-control--;

Column 6, line 49-50, delete "control" and insert therefor --servo-control--;

Column 6, line 51-52, delete "servo control" and insert therefor --servo-control--;

Column 6, line 59, delete "servo control" and insert therefor --servo-control--;

Column 6, line 66, delete "servo control" and insert therefor --servo-control--.

UNITED STATES PATENT AND TRADEMARK OFFICE
CERTIFICATE OF CORRECTION

PATENT NO. : 4,727,322
DATED : FEBRUARY 23, 1988
INVENTOR(S) : Thierry LONCHAMPT ET AL It is certified that error appears in the above-identified patent and that said Letters Patent is hereby corrected as shown below:

Column 7, line 12, delete "parts," and insert therefor --part,--;

Column 7, line 39, delete "servocontrol" and insert therefor --servo-control--.

Signed and Sealed this

Twentieth Day of September, 1988

Attest:

*Attesting Officer*

DONALD J. QUIGG

*Commissioner of Patents and Trademarks*